United States Patent

Vollmer et al.

[11] 3,978,170
[45] Aug. 31, 1976

[54] PROCESS FOR MAKING POLYOLS CONTAINING HALOGEN AND PHOSPHORUS

[75] Inventors: Hartfrid Vollmer, Erftstadt Liblar; Franz-Josef Dany, Erftstadt Lechenich; Joachim Wortmann, Turnich, all of Germany

[73] Assignee: Hoechst Aktiengesellschaft, Frankfurt am Main, Germany

[22] Filed: Nov. 6, 1974

[21] Appl. No.: 521,529

[30] Foreign Application Priority Data
Nov. 9, 1973  Germany............................ 2356034

[52] U.S. Cl............................... 260/968; 260/928; 260/929; 260/930; 260/973; 260/986
[51] Int. Cl.².......................................... C07F 9/09
[58] Field of Search ........... 260/928, 929, 930, 968, 260/973, 986

[56] References Cited
UNITED STATES PATENTS

| | | | |
|---|---|---|---|
| 2,795,609 | 6/1957 | Jensen et al. | 260/973 X |
| 3,147,299 | 9/1964 | Smith et al. | 260/928 X |
| 3,355,436 | 11/1967 | Lutz et al. | 260/928 X |
| 3,764,640 | 10/1973 | Klose | 260/928 X |
| 3,767,732 | 10/1973 | Klose | 260/928 |
| 3,840,622 | 10/1974 | Shim | 260/929 |
| 3,855,360 | 12/1974 | Shim | 260/929 |

OTHER PUBLICATIONS
Houben–Weyl, Methoden der Organischen Chemie, vol. 12/2 (1964), p. 287.

*Primary Examiner*—Richard L. Raymond
*Attorney, Agent, or Firm*—Connolly and Hutz

[57] ABSTRACT

Production of polyols containing halogen and phosphorus. The polyols are more particularly comprised of compounds the following general formula (I)

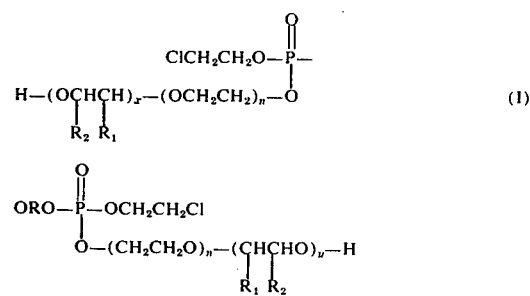

in which R stands for an alkylene radical having from 2 to 6 carbon atoms, which may be halogen-substituted, if desired, a —CH$_2$—CH$_2$—O—CH$_2$—CH$_2$— radical, a phenylene radical or an alkyl- or halogenoalkyl-substituted diphenylene methane radical, $R_1$ and $R_2$, respectively stand for a hydrogen atom, an alkyl radical or a halogen-substituted alkyl radical having from 1 to 4 carbon atoms, $x + y$ stand for a number between 0.1 and 3, and $n$ stands for 1 or 2. The polyols find use as flameproofing agents in plastics, particularly in polyurethane foams.

9 Claims, No Drawings

PROCESS FOR MAKING POLYOLS CONTAINING HALOGEN AND PHOSPHORUS

The present invention relates to polyols containing halogen and phosphorus, which are defined hereinafter, and to a process for making them. The polyols of the present invention have not been described heretofore.

U.S. Pat. No. 3,147,299 describes a a process for making bis-halogenoalkyl-phosphanates of the following general formula

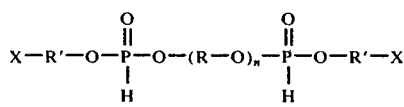

in which R and R' each stand for an alkylene radical having from 2 to 6 carbon atoms, $n$ stands for a whole number within the range 1 and 3, and X stands for a halogen atom, such as chlorine or bromine. As disclosed in this known process, it is possible, for example, to produce ethylene-bis-(2-chloroethylphosphonate) by introducing ethylene glycol dropwise at room temperature into a solution of $PCl_3$ in methylene chloride with evolution of HCl, terminating the reaction, and isolating the resulting ethylene chlorophosphite by subjecting the solvent to evaporation. In a further process step, the ethylene chlorophosphite is reacted with ethylene glycol in a benzenic solution, the solvent is evaporated and ethylene-bis-(2-chloroethylphosphonate) is obtained as an oily liquid residue. The products of the above general formula find use as flameproofing agents in plastics, particularly in polyurethane foams.

We have now found that it is possible for the flameproofing effect of the products described in U.S. Pat. No. 3,147,299 to be improved considerably by substituting a suitable hydrocarbon radical for the hydrogen atoms which are linked to the phosphorus atom, and using, for example, an aryl radical as the radical R in the above general formula.

The present invention relates more particularly to polyols containing halogen and phosphorus of the following general formula (I)

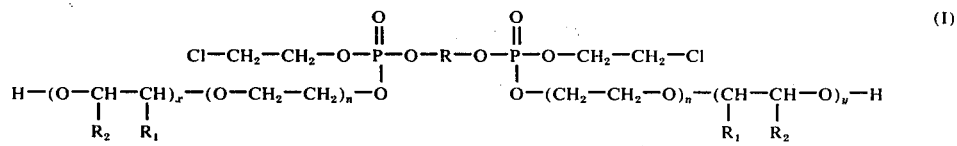

in which R stands for an alkylene radical having from 2 to 6 carbon atoms, which may be halogen-substituted, if desired, a $-CH_2-CH_2-O-CH_2-CH_2-$ radical, a phenylene radical or an alkyl- or halogenoalkyl-substituted diphenylene methane radical, $R_2$ and $R_2$, respectively, stand for a hydrogen atom, an alkyl radical or a halogen-substituted alkyl radical having from 1 to 4 carbon atoms, $x + y$ stand for a number between 0.1 and 3, and $n$ stands for 1 to 2.

The polyols of the present invention preferably comprise the following compounds (a - k):

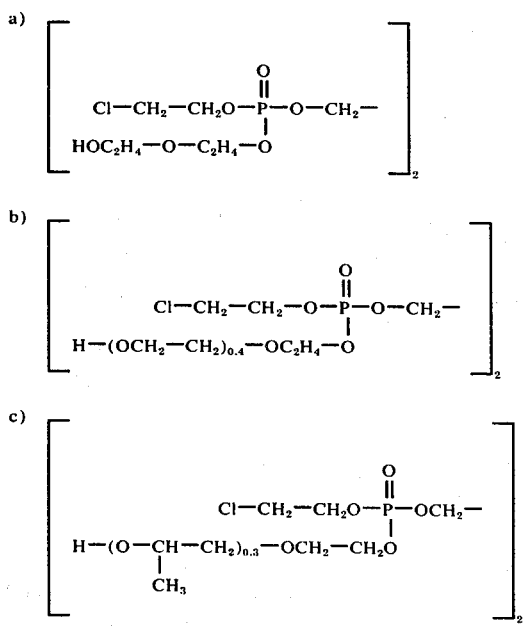

-continued d) 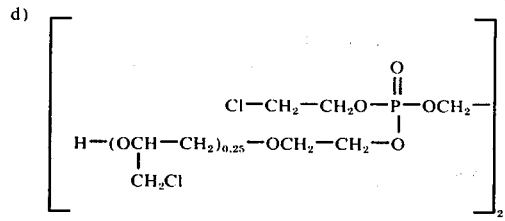

e) 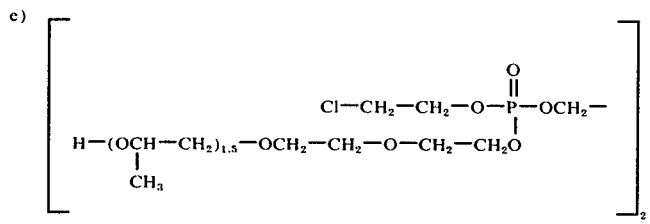

f) 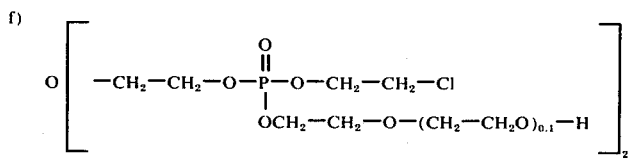

g) 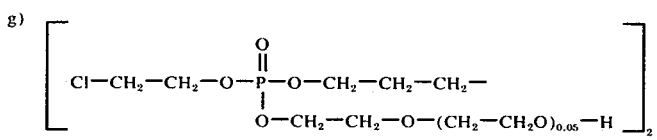

h) 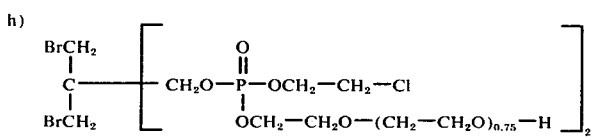

i) 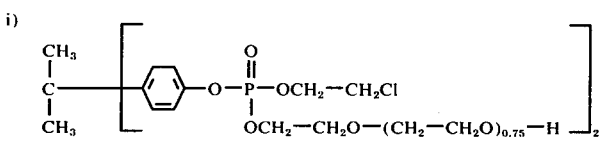

k) 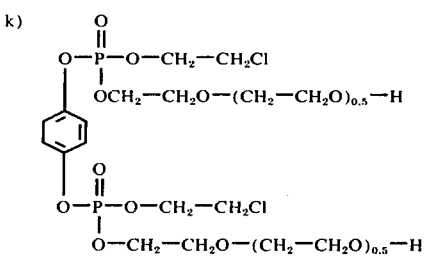

The compounds of the present invention are very viscous, colorless and undistillable liquids.

The invention also relates to a process for making the above polyols containing halogen and phosphorus, which comprises reacting a compound of the general formula (II)

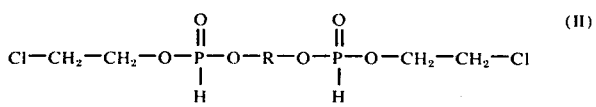

(II)

in which R stands for an alkylene radical having from 2 to 6 carbon atoms, which may be halogen-substituted, if desired, a —$CH_2$—$CH_2$—O—$CH_2$—$CH_2$— radical, a phenylene radical or an alkyl- or halogenoalkyl-substituted diphenylenemethane radical, with at least stoichiometric proportions of chlorine gas, at temperatures within the range about 0° and 5°C, in the presence of a solvent, wherein hydrogen chloride gas is difficulty soluble, and thereby transforming the formula (II) compound into a compound of the general formula (III)

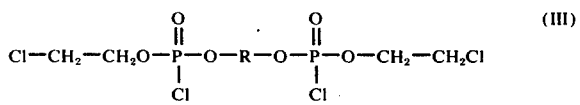

(III)

completing the reaction and removing then the chlorine gas in excess or resulting hydrogen chloride by introducing an inert gas into the reaction solution; and, while the introduction of inert gas is continued, admixing the reaction solution dropwise at temperatures within the range about 15° and 40°C with stoichiometric proportions of a diol of the general formula (IV)

(IV)

in which $n$ stands for 1 or 2; terminating the reaction; distilling off the solvent and subjecting the resulting product of the general formula (V)

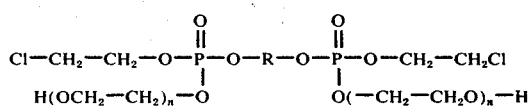

in which $n$ and R have the meanings given hereinabove, to epoxidation with at least stoichiometric proportions of a compound of the general formula (VI)

(VI)

in which $R_1$ and $R_2$, respectively, stand for a hydrogen atom, an alkyl radical or a halogen-substituted alkyl radical having from 1 to 4 carbon atoms, at temperatures within the range about 60° and 140°C for as long a period as necessary to provide for a continuous epoxide reflux; and separating epoxide in excess by distillation or by the introduction of an inert gas.

A preferred embodiment of the present process comprises using as a starting material a compound of general formula (II), in which the substituent R stands for an ethylene or hexamethylene radical or one of the radicals of the following formulae:

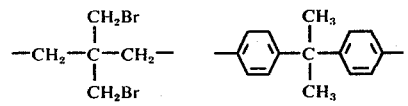

The intermediate compound of general formula (III) should preferably be produced in the presence of methylene chloride or dichloroethane which are solvents absorbing relatively slight proportions of the resulting hydrogen chloride gas byproduct. Fractions of hydrogen chloride, which may have been dissolved therein, can be removed therefrom, for example, by the introduction of nitrogen.

The diol compound of formula (IV) is generally reacted with the phosphoric acid ester chloride (formula III) at room temperature, the diol compound being preferably selected from the ethylene glycol, diethylene glycol, hexane diol, dibromoneopentyl glycol, p,p'-isopropylidene diphenol or hydroquinone.

The expoxidation should preferably be effected with the use of ethylene oxide, propylene oxide or epichlorhydrin. The reaction is more particularly effected at temperatures within the range 80° and 120°C in the presence of a disodium phosphate regulator, which may be used in proportions within the range 0.1 and 0.2 weight %, based on the product of general formula (V).

The formula (II) compound used as starting material in the process of the present invention has already been described in the art and can be made, for example, by the process described in U.S. Pat. No. 3,147,299, Examples 1 and 2.

A particularly beneficial effect encountered in the manufacture of the compounds of the present invention resides in the fact that it is possible for the above reaction to be carried out as a single pot reaction without any need for isolation of intermediary products. The resulting products have an acid number of less than 1 mg of KOH/g of substance. By the appropriate selection of the epoxide compound, it is possible to modify the compounds of the present invention, with respect to their hydroxyl numbers.

The products of the present invention are commercially interesting, very effective reactive flameproofing agents for flammable material, particularly polyurethane foam plastics. They are more effective than compounds of similar constitution, such as the brominated diphosphonate of the following formula:

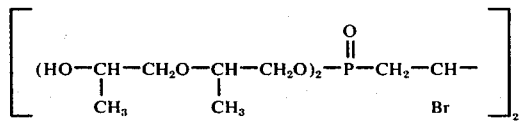

described in U.S. Pat. No. 3,220,961, Example 24.

The following Examples illustrate the invention, which is not limited thereto.

EXAMPLE 1

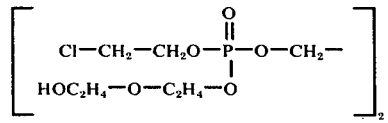

A reactor provided with reflux condenser and stirrer was charged with a solution of 2720 g of $PCl_3$ (19.8 mols) in 4 liters of methylene chloride and the solution was admixed dropwise with agitation and at room temperature with 1224 g of ethylene glycol (19.8 mols). The reaction was terminated after about 2 hours. A further 9.9 mols of ethylene glycol was added in such a manner that the reaction temperature remained within the limits 20° and 25°C. Chlorine was then introduced into the solution at temperatures within the range 0° and 5°C until the solution assumed a green-yellow coloration, which indicated that the reaction was complete. Chlorine in excess and hydrogen chloride, which was found to have been formed, were expelled by the introduction of nitrogen into the solution. The introduction of nitrogen was continued and 1175 g ethylene glycol was added dropwise at room temperature. After HCl ceased to be evolved, the solution was distilled so as to remove the solvent, and a highly viscous colorless liquid was obtained in a yield of 94.5 % of the theoretical.

1000 g of the colorless liquid so obtained was admixed at 80°C with ethylene oxide for as long a period as necessary to have a continuous reflux which indicated that ethylene oxide ceased to be absorbed. Ethylene oxide in excess was expelled with nitrogen.

The product so made was analyzed and the following results were obtained.

|    | Found   | Calculated |
|----|---------|------------|
| P  | 11.7 %  | 11.85%     |
| Cl | 13.7 %  | 13.55 %    |
| OH | 7.9 %   | 6.50 %     |

EXAMPLE 2

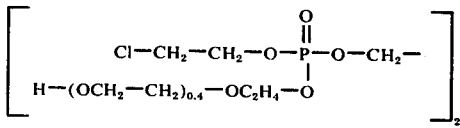

1000 g of the intermediary product of Example 1, which was not epoxidized, was admixed with 2 g of Na$_2$HPO$_4$ and ethylene oxide was then introduced into the liquid at 85°C for as long a period as necessary to have a continuous reflux which indicated that ethylene oxide ceased to be absorbed. Ethylene oxide in excess was expelled by introducing nitrogen into the liquid and 1080 g of a colorless product, which had an acid number of less than 1 mg of KOH/g of substance, was obtained. This corresponded to an absorption rate of 0.8 mole of ethylene oxide per mol of substance. The product was analyzed and the following results were obtained:

|    | Found   | Calculated |
|----|---------|------------|
| P  | 13.3 %  | 13.1 %     |
| Cl | 13.8 %  | 15.0 %     |
| OH | 9.3 %   | 7.3 %      |

EXAMPLE 3

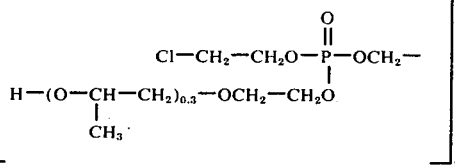

1000 g of the intermediary product of Example 1 was admixed in the manner described in Example 2 with 2g of Na$_2$HPO$_4$ and the whole was reacted with propylene oxide at 80°–100°C The reaction mixture was distilled and thereby freed from its volatile constituents. 1090 g of a colorless product having an acid number of less than 1 mg of KOH/g of substance, was obtained. This corresponded to an absorption rate of about 0.6 mol of propylene oxide per mol of substance.

The product was analyzed and the following results were obtained:

|    | Found   | Calculated |
|----|---------|------------|
| P  | 12.4 %  | 13.1 %     |
| OH | 6.5 %   | 7.5 %      |

EXAMPLE 4

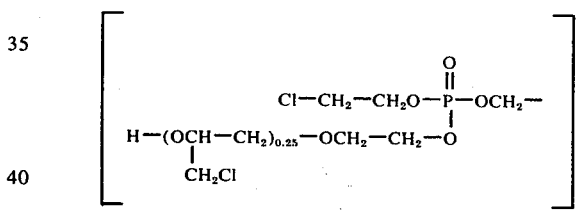

The procedure was the same as that described in Example 2, save that 600 g of the intermediary product of Example 1 was admixed with 1 g of Na$_2$HPO$_4$ and the whole was reacted with 65 g of epichlorhydrin at temperatures within the range 120° and 135°C. Volatile constituents were distilled off from the reaction mixture and 660 of a colorless oil remained behind. This corresponded to the absorption of 0.5 mol of epichlorhydrin per mole of substance. The product had an acid number of 1 mg of KOH/g substance. It was analyzed and the following results were obtained:

|    | Found:  | Calculated: |
|----|---------|-------------|
| P  | 12.6 %  | 12.9 %      |
| Cl | 18.2 %  | 18.2 %      |
| OH | 8.2 %   | 7.2 %       |

EXAMPLE 5

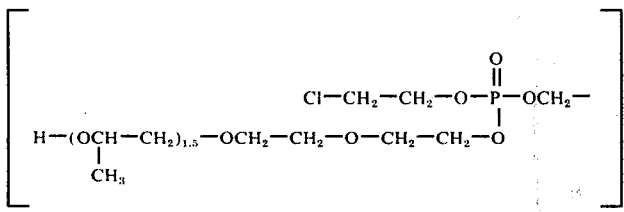

400 g (1.05 mols) of ethylene-bis-(2-chloroethylchlorophosphonate) was dissolved in 0.5 liter of methylene chloride and the solution was reacted with 222 g (2.1 mols) diethylene glycol at 25°C and while introducing nitrogen thereinto. After termination of the reaction, the solvent was distilled off and 540 g of distillation residue was obtained.

485 g of the residue was epoxidized with propylene oxide at about 80°C. 168 g of epoxide was absorbed. This corresponded to an absorption rate of 3 mols of propylene oxide per mol of substance. The epoxidized product had an acid number of 0.06 mg of KOH/g of substance.

The product was analyzed and the following results were obtained:

|    | Found: | Calculated: |
|----|--------|-------------|
| P  | 9.3 %  | 8.95 %      |
| Cl | 9.3 %  | 10.05 %     |
| OH | 5.9 %  | 4.9 %       |

EXAMPLE 6

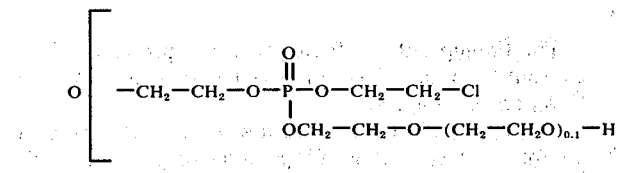

A solution of 10 mols of 2-chloro-1,3,2-dioxaphospholane in 2 l of methylene chloride was admixed with 5 mols of diethylene glycol in such a manner that the reaction temperature did not exceed 20°C. Following this, chlorine gas was introduced until green-yellow coloration of the reaction solution indicated the end of the reaction. Chlorine in excess and hydrogen chloride which was found to have been produced were expelled by means of nitrogen.

570 g (1.3 mols) of the intermediate product dissolved in methylene chloride was reacted, while nitrogen was introduced thereinto, with 165 g of ethylene glycol (2.6 mols) at room temperature, and resulting hydrogen chloride was expelled. The solvent was then distilled off, the residue was admixed with 1 g of Na$_2$HPO$_4$ and epoxidized with ethylene oxide at about 90°C. 12 g of ethylene oxide were found to have been absorbed. This corresponded to an ethylene oxide content of about 0.2 mol. The product so made had an acid number of less than 1 mg of KOH/g of substance.

The product was analyzed and the following results were obtained:

|    | Found:  | Calculated: |
|----|---------|-------------|
| P  | 11.9 %  | 12.35 %     |
| Cl | 13.2 %  | 14.3 %      |
| OH | 8.2 %   | 7.0 %       |

EXAMPLE 7

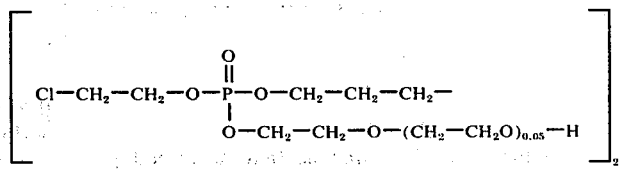

The procedure was the same as that described in Example 6, save that 1,6-hexane diol was substituted for diethylene glycol. Ethylene oxide was absorbed at a rate of about 0.1 per mol of substance. The product obtained had an acid number of less than 1 mg of KOH/g of substance.

It was analyzed and the following results were obtained:

|    | Found: | Calculated: |
|----|--------|-------------|
| P  | 9.4 %  | 10.2 %      |
| Cl | 13.5 % | 12.0 %      |

EXAMPLE 8

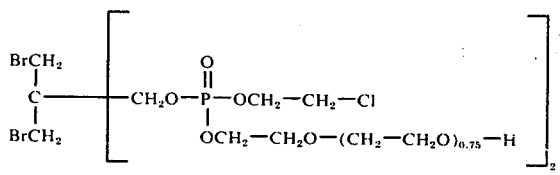

The procedure was the same as that described in Example 6, but dibromoneopentyl glycol was substituted for diethylene glycol. Ethylene oxide was absorbed at a rate of about 1.5 mols per mol of substance.

The product so made was analyzed and the following results were obtained:

|   | Found: | Calculated: |
|---|--------|-------------|
| P  | 8.0 % | 8.8 % |
| Cl | 9.2 % | 10.1 % |

EXAMPLE 9

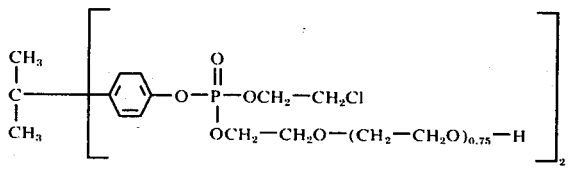

The procedure was the same as that described in Example 6, save that 228 g of p,p'-isopropylidene diphenol (1 mole) was dissolved in methylene chloride and 253 g of 2-chloro-1,3,2,-dioxaphospholane (2 mols) was added dropwise to the solution. As the reaction proceeded, the solution became clear. The reaction temperature was within the range 25° and 35°C. At temperatures within the range −5° and +5°C, chlorine gas was introduced into the solution until it commenced to assume a yellow coloration.

0.8 mol of the intermediary product dissolved in methylene chloride was reacted at room temperature with 1.6. mols of ethylene glycol while nitrogen was introduced thereinto. Following this, the solvent was distilled off and the whole was epoxidized at 100°C with ethylene oxide with the addition of 1 g of Na$_2$H-PO$_4$. Ethylene oxide was absorbed at a rate of 1.5 mols per mol of substance.

The product so made has an acid number of less than 1 mg of KOH/g substance.

It was analyzed and the following results were obtained:

|   | Found: | Calculated: |
|---|--------|-------------|
| P  | 8.9 % | 9.3 % |
| Cl | 11.8 % | 10.3 % |
| OH | 7.6 % | 5.1 % |

EXAMPLE 10

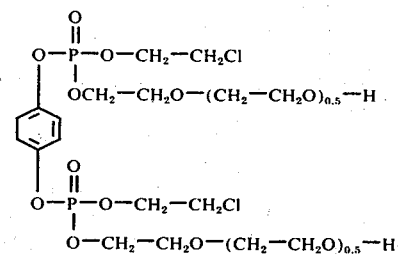

The procedure was the same as that described in Example 9, save that hydroquinone was substituted for p,p'-isopropylidine diphenol. Ethylene oxide was absorbed at a rate of 1 mol per mol of substance.

The product so made had an acid number of less than 1 mg of KOH/g of substance.

It was analyzed and the following results were obtained:

|   | Found: | Calculated: |
|---|--------|-------------|
| P  | 11.7 % | 11.7 % |
| Cl | 12.7 % | 13.4 % |
| OH | 7.5 % | 6.5 % |

The flameproofing efficiency of the products of the present invention was compared with that of known flameproofing agents.

More particularly the present products were tested as to their flameproofing efficiency in polyurethane soft foams. To this end, they were incorporated with polyurethane soft foams and the foams were subjected to burn-up tests (ASTM D 1692-59 T). Comparative tests were made on known flameproofing agents, such as tris-(dichloropropyl)-phosphate, tris-(dibromopropyl)-phosphate, tetra-(dipropylene-glycol)-2,3-dibromobutene-1,4-diphosphonate and ethylene-bis-(2-chloroethyl)-phosphonate. The polyurethane soft foams were made as follows:

100g of a partially branched polyetherpolyol based on propylene oxide and having a hydroxyl number of 46 mg of KOH/g, a molecular weight of 3500, a viscosity of 575 centipoises at 25°C and a ratio of primary to secondary OH-groups of 22:78 (Desmophen 3800, a product of Bayer, Leverkusen),
10g of flameproofing agent,
4.2g of water,
0.12g of triethylene diamine,
0.2g of tin-II-octoate, and
1.0g of a polyethylene-polydimethylsiloxane block copolymer having a viscosity of 1200 centistokes at 25°C and a unit weight of 1.03 (L 540, a product of Union Carbide)

were blended together, and 53.2 g of toluylene diisocyanate (a 80:20 blend of the 2,4- and 2,6-isomers) was added to the blend so made, with rapid agitation. After about 20 seconds, the blend commenced foaming. It was poured in a container. After a certain expansion period, the foam began to harden. It was hard after storage for 15 minutes at 80°C. The foams so made were tested as to their flammability (ASTM D 1692-59 T). Both freshly prepared foams and foams artificially aged by 7-day storage at 80°C and 100 percent relative atmospheric moisture were tested. The results obtained are indicated in the following table:

TABLE:

| Flameproofing agent | I | II | III |
|---|---|---|---|
| A | 90 | SE 34 mm, 29 sec | SE 26 mm, 9 sec |
| B | 92 | SE 30 mm, 18 sec | SE 26 mm, 11 sec |
| C | 84 | SE 41 mm, 23 sec | SE 40 mm, 19 sec |
| D | 95 | SE 38 mm, 29 sec | SE 32 mm, 9 sec |
| E | 85 | SE 64 mm, 44 sec | B 114 mm/min. |
| F | 90 | SE 46 mm, 37 sec | SE 62 mm, 41 sec |
| G | 110 | SE 42 mm, 28 sec | SE 69 mm, 43 sec |
| H | 70 | SE 30 mm, 16 sec | SE 45 mm, 23 sec |

In the above Table, the various abbreviations have the following meanings:

Flameproofing agents
A: Product of Example 3
B: Product of Example 4
C: Product of Example 8
D: Product of Example 9
E: Tris-(dichloropropyl)-phosphate
F: Tris-(dibromopropyl)-phosphate
G: Tetra-(dipropyleneglycol)-2,3-dibromobutene-1,4-diphosphonate (U.S. Pat. No. 3,220,961, Example 4)
H: Ethylene-bis-(2-chloroethyl)-phosphite (U.S. Pat. No. 3,147,299, Example 2)
Column I: Expansion period of foam in seconds
Column II: Burn-up test (ASTM D 1962-59 T) immediately after preparation of foam.
Column III: Burn-up test (ASTM D 1692-59 T) after storage of foam for 7 days at 80°C and 100% relative atmospheric moisture.
SE: Self-extinction after . . . mm and . . . seconds
B: Burn-up rate in mm per minute As can be seen, the foams rendered flameproof with the agents of the present invention all have a shorter burn-up period until self-extinction than the foams rendered flameproof with known flameproofing agents. In other words, the flameproofing agents of the present invention compare favorably with the prior art agents.

We claim:
1. A process for making polyols containing halogen and phosphorus of the following general formula (I)

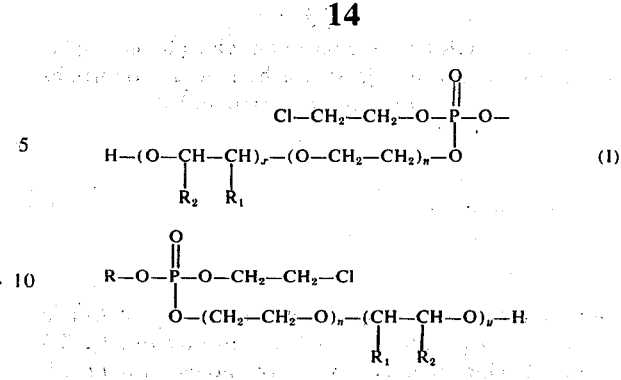

in which R stands for an alkylene radical having from 2 to 6 carbon atoms, which may be halogen-substituted, if desired, a —CH$_2$—CH$_2$—O—CH$_2$—CH$_2$— radical, a phenylene radical or a alkyl- or halogenoalkyl-substituted diphenylene methane radical, R$_1$ and R$_2$, respectively, stand for a hydrogen atom, an alkyl radical or a halogen-substituted alkyl radical having from 1 to 4 carbon atoms, $x + y$ stand for a number between 0.1 and 3, and $n$ stands for 1 or 2, which process comprises reacting a compound of the general formula (II)

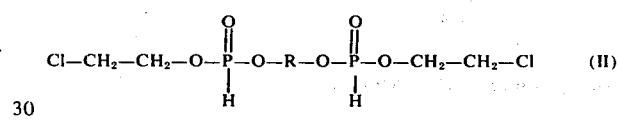

in which R stands for a alkylene radical or a halogen-substituted alkylene radical having from 2 to 6 carbon atoms, a —CH$_2$—CH$_2$—O—CH$_2$—CH$_2$— radical, a phenylene radical or an alkyl- or halogenoalkyl-substituted diphenylenemethane radical, with at least stoichiometric proportions of chlorine gas, at temperatures within the range about 0° and 5°C, in the presence of a solvent, wherein hydrogen chloride gas is difficultly soluble, and thereby transforming the formula (II) into a general formula (III) compound

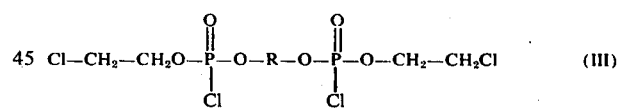

completing the reaction and removing then the chlorine gas in excess or resulting hydrogen chloride by introducing an inert gas into the reaction solution; and, while the introduction of inert gas is continued, admixing the reaction solution dropwise at temperatures within the range of about 15° and 40°C with stoichiometric porportions of a diol of the general formula (IV)

in which $n$ stands for 1 or 2; terminating the reaction; distilling off the solvent and subjecting the resulting product of the general formula (V)

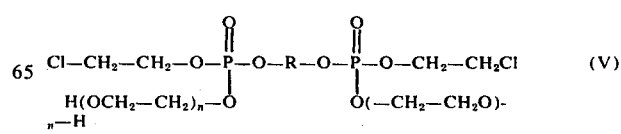

in which n and R have the meanings given hereinabove, to epoxidation with at least stoichiometric proportions of a compound of the general formula (VI)

in which $R_1$ and $R_2$, respectively, stand for a hydrogen atom, an alkyl radical or a halogen-substituted alkyl radical having from 1 to 4 carbon atoms, at temperatures within the range about 60° and 140°C for as long a period as necessary to provide for a continuous epoxide reflux, and separating epoxide in excess by distillation or by the introduction of an inert gas.

2. The process as claimed in claim 1 wherein R stands for an ethylene radical or hexamethylene radical, a radical of the formula

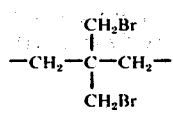

or a radical of the formula

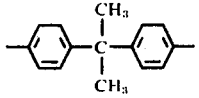

3. The process as claimed in claim 1, wherein the difficulty soluble solvent for hydrogen chloride is methylene chloride or dichloroethane.

4. The process as claimed in claim 1, wherein nitrogen is used as the inert gas.

5. The process as claimed in claim 1, wherein the compounds of formula (III) and (IV) are reacted at room temperature.

6. The process as claimed in claim 1, wherein the diol is ethylene glycol or diethyleneglycol.

7. The process as claimed in claim 1, wherein the epoxide is ethyleneoxide, propylene oxide or epichlorhydrin.

8. The process as claimed in claim 1 wherein the epoxidation reaction is carried out at temperatures within the range of 80° and 120°C in the presence of disodium phosphate as a regulator.

9. The process as claimed in claim 1, wherein the regulator is used in proportions within the range 0.1 and 0.2 weight %, based on the formula (V) compound.

* * * * *